United States Patent
Byrne et al.

(10) Patent No.: US 9,267,241 B2
(45) Date of Patent: *Feb. 23, 2016

(54) PROCESS FOR MANUFACTURING ABSORBENT SANITARY PAPER PRODUCTS

(71) Applicant: The Procter & Gamble Company, Cincinnati, OH (US)

(72) Inventors: Thomas Timothy Byrne, West Chester, OH (US); Kevin Benson McNeil, Loveland, OH (US); Kathryn Christian Kien, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 4 days.

This patent is subject to a terminal disclaimer.

(21) Appl. No.: 14/718,156

(22) Filed: May 21, 2015

(65) Prior Publication Data

US 2015/0267351 A1    Sep. 24, 2015

Related U.S. Application Data

(63) Continuation of application No. 14/168,634, filed on Jan. 3, 2014, now Pat. No. 9,051,693.

(51) Int. Cl.
*D21H 27/30* (2006.01)
*D21H 27/32* (2006.01)
*D21H 27/02* (2006.01)
*D21H 27/00* (2006.01)
(Continued)

(52) U.S. Cl.
CPC ............... *D21H 27/02* (2013.01); *D04H 1/70* (2013.01); *D04H 11/00* (2013.01); *D21H 11/04* (2013.01); *D21H 27/007* (2013.01); *D21H 27/30* (2013.01); *D21H 27/32* (2013.01)

(58) Field of Classification Search
CPC ....... D21H 11/00; D21H 15/00; D21H 27/30; D21H 27/32; D21H 5/2642; D21H 5/2664; D04H 11/00; D04H 1/74; D04H 3/12; D04H 3/16; B05D 1/16; B05D 7/04; B32B 5/022; B32B 7/12; B32B 2432/00; B32B 2555/00; B32B 33/00; D06N 3/004
See application file for complete search history.

(56) References Cited

U.S. PATENT DOCUMENTS 3,322,606 A * 5/1967 Koller .............................. 428/95
3,459,579 A * 8/1969 Newman ....................... 427/200
(Continued)

OTHER PUBLICATIONS

U.S. Appl. No. 14/168,625, filed Jan. 30, 2014, McNeil, et al.
(Continued)

*Primary Examiner* — Jose Fortuna
(74) *Attorney, Agent, or Firm* — Peter D. Meyer

(57) ABSTRACT

A method of manufacturing an absorbent sanitary paper product having a machine direction, a cross-machine direction orthogonal and co-planar thereto, and a Z-direction orthogonal to both the machine- and cross-machine directions is disclosed. The method provides the steps of: providing a first and second network of fibers each having opposing first and second sides where each fiber of the first network of fibers has a longitudinal axis generally disposed within the plane comprising the machine- and cross-machine-directions; applying a first bonding layer to one of the first and second sides of the first network of fibers; applying a first and second second network of fibers to the first bonding layer; and, placing the first and second network of fibers into face-to-face contacting engagement.

10 Claims, 4 Drawing Sheets

(51) Int. Cl.
*D04H 1/70* (2012.01)
*D04H 11/00* (2006.01)
*D21H 11/04* (2006.01)

(56) References Cited

U.S. PATENT DOCUMENTS

| | | | |
|---|---|---|---|
| 3,496,054 A * | 2/1970 | Baigas, Jr. | 428/89 |
| 3,772,131 A * | 11/1973 | Triplett | 428/90 |
| 3,903,331 A * | 9/1975 | Klein | 427/206 |
| 3,961,116 A * | 6/1976 | Klein | 428/90 |
| 3,979,538 A * | 9/1976 | Gilman et al. | 428/90 |
| 3,984,898 A * | 10/1976 | Matsumura et al. | 425/81.1 |
| 3,993,806 A * | 11/1976 | Athey | 427/206 |
| 4,362,773 A * | 12/1982 | Shikinami | 428/90 |
| 4,418,106 A * | 11/1983 | Landler et al. | 428/89 |
| 4,430,372 A * | 2/1984 | Knoke et al. | 428/90 |
| 4,465,723 A * | 8/1984 | Knoke et al. | 428/90 |
| 4,529,480 A | 7/1985 | Trokhan | |
| 4,687,527 A * | 8/1987 | Higashiguchi | 156/72 |
| 5,047,103 A | 9/1991 | Abrams et al. | |
| 5,108,777 A | 4/1992 | Laird | |
| 5,458,915 A * | 10/1995 | Yamamoto | 427/143 |
| 6,770,581 B1 * | 8/2004 | DeMott et al. | 442/312 |
| 6,846,383 B2 | 1/2005 | Tirimacco | |
| 7,410,682 B2 * | 8/2008 | Abrams | 428/90 |
| 7,749,589 B2 * | 7/2010 | Abrams | 428/90 |
| 7,811,613 B2 | 10/2010 | Vinson et al. | |
| 7,851,391 B2 | 12/2010 | Bond et al. | |
| 7,918,951 B2 | 4/2011 | Lorenz et al. | |
| 8,007,889 B2 | 8/2011 | Abrams et al. | |
| 8,303,560 B2 | 11/2012 | Cecconi et al. | |
| 8,522,711 B2 | 9/2013 | McNeil et al. | |
| 9,051,693 B1 * | 6/2015 | Byrne et al. | |
| 2001/0008672 A1 * | 7/2001 | Norvell et al. | 428/90 |
| 2004/0053001 A1 * | 3/2004 | Abrams | 428/90 |
| 2004/0058120 A1 | 3/2004 | Abrams | |
| 2004/0081791 A1 | 4/2004 | Abrams | |
| 2004/0229008 A1 | 11/2004 | Hoying | |
| 2006/0026778 A1 * | 2/2006 | Lion | 8/488 |
| 2006/0123573 A1 | 6/2006 | Rivera et al. | |
| 2008/0289129 A1 * | 11/2008 | Kizuka et al. | 15/118 |
| 2008/0318487 A1 * | 12/2008 | Pedoja | 442/382 |
| 2009/0035515 A1 * | 2/2009 | Cecconi et al. | 428/137 |
| 2009/0221982 A1 * | 9/2009 | Cecconi et al. | 604/385.3 |
| 2010/0112273 A1 * | 5/2010 | Pedoja | 428/91 |
| 2013/0115408 A1 * | 5/2013 | Abrams | 428/86 |
| 2015/0211185 A1 * | 7/2015 | Kien | D04H 1/70 428/340 |
| 2015/0211186 A1 * | 7/2015 | McNeil | D04H 1/70 428/113 |
| 2015/0211187 A1 * | 7/2015 | McNeil | D21H 27/007 428/201 |
| 2015/0267351 A1 * | 9/2015 | Byrne | D21H 11/04 162/109 |

OTHER PUBLICATIONS

U.S. Appl. No. 14/168,596, filed Jan. 30, 2014, Kien, et al.
U.S. Appl. No. 14/168,605, filed Jan. 30, 2014, McNeil, et al.
U.S. Appl. No. 14/168,634, filed Jan. 30, 2014, Byrne, et al.
PCT International Search Report, mailed Apr. 29, 2015, 121 pages.

* cited by examiner

PROCESS FOR MANUFACTURING ABSORBENT SANITARY PAPER PRODUCTS

FIELD OF THE INVENTION

This invention relates, in general, to absorbent sanitary paper products. More specifically, it relates to absorbent sanitary paper products having a first network of fibrous material having a second network of a fibrous material adhesively attached thereto.

BACKGROUND OF THE INVENTION

Absorbent sanitary paper products, such as bath tissue, facial tissue, and paper towels are commonly used in households, businesses, restaurants, shops, and the like.

Manufacturers of absorbent paper products understand that consumers desire absorbent sanitary paper products to be soft to the touch. Softness is a complex tactile impression elicited by an absorbent sanitary paper product when it is stroked against human skin. The purpose of being soft is so that these absorbent sanitary paper products can be used to cleanse the skin without causing irritation.

Accordingly, absorbent sanitary paper products, such as bath tissue and paper towel products, that promote softness, comfort, and/or cleaning without providing any performance-impairing sacrifices have long been the goal of the engineers and scientists devoted to improving absorbent sanitary paper products. There have been numerous attempts to reduce abrasive effects such as improving the softness of absorbent sanitary paper products as well as increase the absorbency thereof.

Although somewhat desirable for towel products, softness can be a particularly important property for facial and bath tissue products. Such tactile perceivable softness can be characterized by, but is not limited to, friction, flexibility, and smoothness, as well as subjective descriptors, such as lubricious, velvet, silk or flannel, which imparts a lubricious feel to tissue.

Another important physical property related to softness is generally considered by those skilled in the art to be the strength of the absorbent sanitary paper products. Strength is the ability of the absorbent sanitary paper products, and its constituent webs, to maintain physical integrity and to resist tearing, bursting, and shredding under use conditions. Achieving a high softening potential without degrading strength has long been an object of workers in the field of the present invention.

Accordingly, it would be desirable to be able to provide an absorbent sanitary paper product that provides higher tactile softness while maintaining strength at least at par with currently available commercial absorbent sanitary paper products.

SUMMARY OF THE INVENTION

One embodiment of the present disclosure provides for a method of manufacturing an absorbent sanitary paper product having a machine direction, a cross-machine direction orthogonal and co-planar thereto, and a Z-direction orthogonal to both the machine- and cross-machine directions. The method comprising the steps of: providing a first first network of fibers having opposing first and second sides, each fiber of the first first network of fibers having a longitudinal axis generally disposed within the plane comprising the machine- and cross-machine-directions; providing a second first network of fibers having opposing first and second sides, each fiber of the second first network of fibers having a longitudinal axis generally disposed within the plane comprising the machine- and cross-machine-directions; applying a bonding layer to the first side of the first first network of fibers; applying a first second network of fibers to the bonding layer, each individual fiber comprising the second network of fibers having a longitudinal axis generally disposed in the Z-direction; applying a second second network of fibers to the bonding layer, each individual fiber comprising the second second network of fibers having a longitudinal axis generally disposed in the Z-direction, the first second network of fibers and the second second network of fibers being different; and, placing the second side of the first first network of fibers and the second side of the second first network of fibers into contacting engagement.

Another embodiment of the present disclosure provides for a method of manufacturing an absorbent sanitary paper product having a machine direction, a cross-machine direction orthogonal and co-planar thereto, and a Z-direction orthogonal to both the machine- and cross-machine directions. The method comprising the steps of: providing a first first network of fibers having opposing first and second sides, each fiber of the first first network of fibers having a longitudinal axis generally disposed within the plane comprising the machine- and cross-machine-directions; providing a second first network of fibers having opposing first and second sides, each fiber of the second first network of fibers having a longitudinal axis generally disposed within the plane comprising the machine- and cross-machine-directions; applying a first bonding layer to the first side of the first first network of fibers; applying a first second network of fibers to a first region of the first bonding layer, each individual fiber comprising the first second network of fibers having a longitudinal axis generally disposed in the Z-direction; applying a second second network of fibers to a second region of the first bonding layer, each individual fiber comprising the second second network of fibers having a longitudinal axis generally disposed in the Z-direction, the first region of the bonding layer being disposed adjacent the second region of the bonding layer; and, placing the second side of the first first network of fibers and the second side of the second first network of fibers into contacting engagement.

Still another embodiment of the present disclosure provides for a method of manufacturing an absorbent sanitary paper product having a machine direction, a cross-machine direction orthogonal and co-planar thereto, and a Z-direction orthogonal to both the machine- and cross-machine directions. The method comprises the steps of: providing a first network of fibers, each fiber of the first network of fibers having a longitudinal axis generally disposed within the plane comprising the machine- and cross-machine-directions; applying a first bonding layer to one of the first and second sides of the first network of fibers; and applying a first second network of fibers to the first bonding layer, the first second network of fibers comprising a combination of a first plurality of fibers and a second plurality of fibers, the first and second pluralities of fibers being different.

DETAILED DESCRIPTION OF THE INVENTION

As used herein, the term 'machine direction' refers to the direction of travel of a web material through any processing equipment. The term 'cross-machine direction' is orthogonal and co-planar thereto. The term 'Z-direction' is orthogonal to both the machine and cross-machine directions.

Figure 1:
FIG. 1 is a photomicrograph showing the surface of an exemplary absorbent sanitary paper product of the present disclosure detailing the first network of fibers and second network of fibers applied to a surface of the first network of fibers in a discontinuous pattern as discussed herein.

Referring to FIG. 1, as used herein, the terms "absorbent sanitary paper product" and/or "absorbent sanitary paper material" 10 are used interchangeably to refer to sheets of paper characterized by having a first network of fibers 20 (where the longitudinal axis of the constituent fibers forming the first network of fibers 20 are generally disposed in the plane comprising the machine and/or cross-machine directions) and having a second network of fibers 30 (where the longitudinal axis of the fibers comprising the second network of fibers 30 are generally disposed in the Z-direction) bonded, with or without an adhesive, thereto.

Preferably, an absorbent sanitary paper product 10 of the present disclosure is generally a soft, low density material that is suitable for use as a wiping implement for post-urinary and post-bowel movement cleaning (e.g., bath tissue), for otorhinolaryngological discharges (e.g., facial tissue), and multi-functional absorbent and cleaning uses (e.g., absorbent paper towels).

The absorbent sanitary paper products 10 of the present disclosure may be convolutely wound about a core (or convolutely wound about itself without a core or cut, folded, and/or stacked) to form dispensable rolls or packages of absorbent sanitary paper products. Such dispensable rolls of absorbent sanitary paper product may be provided as a plurality of connected (or even unconnected), perforated (or separate) sheets of web material, that are separably and/or separately dispensable from adjacent sheets.

Further, absorbent sanitary paper products 10 of the present disclosure may comprise additives such as softening agents, temporary wet strength agents, permanent wet strength agents, bulk softening agents, lotions, silicones, wetting agents, latexes, especially surface-pattern-applied latexes, dry strength agents such as carboxymethylcellulose and starch, and other types of additives that one of skill in the art would recognize as suitable for inclusion in and/or on absorbent sanitary paper products 10.

First Network of Fibers

The term 'first network of fibers' can refer generally to a web material that can be made by any process suitable for the manufacture of absorbent sanitary paper products 10. No limitation on the process for the manufacture of absorbent sanitary paper products 10 or other similar consumer bath tissue and paper toweling products is made.

In one non-limiting example, a first network of fibers 20 can be made by a process that generally comprises the steps of forming an aqueous papermaking furnish, depositing the aqueous papermaking furnish on a foraminous surface, such as a Fourdrinier wire, and removing the water from the furnish (e.g., by gravity or vacuum-assisted drainage), forming an embryonic web, and transferring the embryonic web from the forming surface to a transfer surface traveling at a lower speed than the forming surface. The web can then be transferred to a fabric upon which it is through air dried to a final dryness after which it is wound upon a reel.

The first network of fibers 20 of the present disclosure preferably comprises papermaking fibers of both hardwood and softwood types wherein at least about 50% of the papermaking fibers are hardwood and at least about 10% are softwood. The hardwood and softwood fibers are most preferably isolated by relegating each to separate layers wherein the tissue comprises an inner layer and at least one outer layer. Another embodiment of the first network of fibers 20 of the present disclosure can utilize multiple papermaking furnishes to provide first network of fibers 20 with a content of at least about 80% hardwood.

Additionally, the first network of fibers 20 can include filaments and/or materials produced by known wet, solution, and dry filament spinning processes that are typically referred to as nonwoven processes. In one example, the filament spinning process is a meltblowing process where filaments are provided from a meltblow die (a filament source). Further processing of the fibrous structure may be carried out such that a finished fibrous structure is formed. For example, the finished fibrous structure is a fibrous structure that is wound on a reel at the end of a fibrous structure making process. The finished fibrous structure may subsequently be converted into a finished product, e.g. a sanitary tissue product.

A filament is an elongate particulate having a length greatly exceeding its average diameter, i.e. a length to average diameter ratio of at least about 10. In one example, the filament is a single filament rather than a yarn, which is a strand of filaments twisted together along their lengths. Filaments are typically considered continuous or substantially continuous in nature especially with respect to the fibrous structure in which they are present. Filaments are relatively longer than fibers. Non-limiting examples of filaments include meltblown and/or spunbond filaments. Non-limiting examples of polymers that can be spun into filaments include natural polymers, such as starch, starch derivatives, cellulose, such as rayon and/or lyocell, and cellulose derivatives, hemicellulose, hemicellulose derivatives, and synthetic polymers including, but not limited to thermoplastic polymer filaments, such as polyesters, nylons, polyolefins such as polypropylene filaments, polyethylene filaments, and biodegradable thermoplastic fibers such as polylactic acid filaments, polyhydroxyalkanoate filaments, polyesteramide filaments and polycaprolactone filaments. The filaments may be mono-component and/or multi-component.

The first network of fibers 20 can be provided as a single-ply comprising one ply of creped or un-creped web material. Any particular ply of creped or un-creped web material can be substantially homogeneous in nature or it can be multi-layered. The first network of fibers 20 can also be provided as a multi-ply web material that is comprised of more than one ply of creped or un-creped web material. In any regard, the plies of an exemplary first network of fibers 20 can be substantially homogeneous in nature or they can be multi-layered web materials.

The first network of fibers 20 can also be prepared from two or more layers of aqueous paper making furnish that are preferably comprised of different fiber types. In this case, the fibers can be provided as relatively long softwood and relatively short hardwood fibers. The layers can preferably be formed from the deposition of separate streams of dilute fiber slurries upon one or more endless foraminous surfaces. If the individual layers are initially formed on separate foraminous surfaces, the resulting layers can then be subsequently combined when wet to form a multi-layered first network of fibers 20.

A Yankee dryer is a large diameter, generally 8-20 foot diameter drum designed to be pressurized with steam to provide a hot surface for completing the drying of paper webs at the end of a papermaking process. The first network of fibers 20 can be transferred in a semi-dry condition to the surface of the Yankee dryer for the through air drying (TAD) process to be completed.

The first network of fibers 20 of the present disclosure can be creped. This means that the first network of fibers 20 can be produced on a papermaking machine culminating with a Yankee dryer to which a partially dried web material that will form the first network of fibers 20 is adhered and upon which it is dried and from which it is removed by the action of a flexible creping blade.

Creping is a means of mechanically compacting the first network of fibers 20 (or any web material) in the machine direction. The creping action can result in an increase in basis weight (mass per unit area) of the first network of fibers 20 as well as dramatic changes in many physical properties of the first network of fibers 20, particularly when measured in the machine direction. Creping is generally accomplished with a flexible blade against a Yankee dryer in an on-machine operation.

While the characteristics of creped web materials that form the first network of fibers 20, particularly when the creping process is preceded by methods of pattern densification, are preferred for forming the first network of fibers 20 of the present disclosure, un-creped web substrates can also be a satisfactory substitute and the practice of the present disclosure using un-creped web materials are specifically incorporated within the scope of the present disclosure. One form of a first network of fibers 20 is an un-creped tissue paper.

An un-creped tissue paper generally refers to a web substrate that is non-compressively dried, most preferably by TAD. The resultant TAD web materials forming the first network of fibers 20 can be pattern densified so that zones of relatively high density are dispersed within a high bulk field. This can include pattern densified web materials where zones of relatively high density are continuous and the high bulk field is discrete.

An exemplary un-creped tissue paper web suitable for the first network of fibers 20 can be formed by an embryonic web which is transferred from the foraminous forming carrier upon which it is laid, to a slower moving, high fiber support transfer fabric carrier. The web is then transferred to a drying fabric upon which it is dried to a final dryness. Such webs can offer some advantages in surface smoothness compared to creped paper webs.

Web materials suitable for forming the first network of fibers 20 are preferably generally comprised of papermaking fibers. Small amounts of chemical functional agents such as wet strength or dry strength binders, retention aids, surfactants, size, chemical softeners, and crepe facilitating compositions are frequently included but these are typically only used in minor amounts. The papermaking fibers most frequently used in tissue papers that form the first network of fibers 20 are virgin chemical wood pulps. Additionally, filler materials may also be incorporated into the tissue papers of the present invention.

If desired, softening agents such as quaternary ammonium compounds can be added to the papermaking slurry that forms the first network of fibers 20. Exemplary quaternary compounds may have the formula:

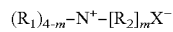

where:

m is 1 to 3;

$R_1$ is a $C_1$-$C_6$ alkyl group, hydroxyalkyl group, hydrocarbyl or substituted hydrocarbyl group, alkoxylated group, benzyl group, or mixtures thereof;

$R_2$ is a $C_{14}$-$C_{22}$ alkyl group, hydroxyalkyl group, hydrocarbyl or substituted hydrocarbyl group, alkoxylated group, benzyl group, or mixtures thereof; and $X^-$ is any softener-compatible anion suitable for use in the present disclosure.

Preferably, each $R_1$ is methyl and $X^-$ is chloride or methyl sulfate. Preferably, each $R_2$ is $C_{16}$-$C_{18}$ alkyl or alkenyl; most preferably each $R_2$ is straight-chain $C_{18}$ alkyl or alkenyl. Optionally, the $R_2$ substituent can be derived from vegetable oil sources.

It is anticipated that wood pulp in all its varieties will normally comprise webs suitable for the first network of fibers 20 having utility in this disclosure. However, other cellulose fibrous pulps, such as cotton linters, bagasse, trichomes, rayon, starches, and the like can be used and none are disclaimed. Wood pulps useful herein include chemical pulps such as, sulfite and sulfate (sometimes called Kraft) pulps as well as mechanical pulps including for example, ground wood, ThermoMechanical Pulp (TMP) and Chemi-Thermo-Mechanical Pulp (CTMP). Pulps derived from both deciduous and coniferous trees can be used.

Hardwood pulps and softwood pulps, as well as combinations of the two, may be employed as suitable fibers for the first network of fibers 20 of the present disclosure. The term "hardwood pulps" as used herein refers to fibrous pulp derived from the woody substance of deciduous trees (angiosperms), whereas "softwood pulps" are fibrous pulps derived from the woody substance of coniferous trees (gymnosperms). Blends of hardwood Kraft pulps, especially eucalyptus, and northern softwood Kraft (NSK) pulps are particularly suitable for making the tissue webs of the present invention. An exemplary embodiment of the present disclosure comprises the use of layered tissue webs to form the first network of fibers 20. Most preferably, hardwood pulps such as eucalyptus are used for outer layer(s) and wherein northern softwood Kraft pulps are used for the inner layer(s). Also applicable to the present disclosure are fibers derived from recycled paper, which may contain any or all of the above categories of fibers.

Other materials can be added to an aqueous papermaking furnish or an embryonic web to impart other characteristics to the first network of fibers 20 and/or the resulting absorbent sanitary paper products 10 that do not significantly and adversely affect the desired softness and strength, or characteristics of the first network of fibers 20 and/or absorbent sanitary paper products 10 of the present disclosure. The following materials are expressly included, but their inclusion is not offered to be all-inclusive. Other materials can be included as well so long as they do not interfere or counteract the advantages of the present invention.

If permanent wet strength is desired, the group of chemicals: including polyamide-epichlorohydrin, polyacrylamides, styrene-butadiene latices; insolubilized polyvinyl alcohol; urea-formaldehyde; polyethyleneimine; chitosan polymers and mixtures thereof can be added to the papermaking furnish or to the embryonic web that forms the first network of fibers 20. Polyamide-epichlorohydrin resins can be of particular utility.

If it is desired to provide a first network of fibers 20 and/or an absorbent sanitary paper products 10 with limited strength when wet because of the need for disposal through toilets into septic or sewer systems, binder materials can be chosen from the group consisting of dialdehyde starch or other resins with aldehyde functionality such as Co-Bond® 1000® offered by National Starch and Chemical Company, Parez® 750® offered by Cytec of Stamford, Conn.

If enhanced absorbency is needed, surfactants may be used to treat the first network of fibers 20 and/or absorbent sanitary paper products 10 of the present invention. The level of surfactant, if used, can preferably range from about 0.01% to about 2.0% by weight, based on the dry fiber weight of the tissue paper. Surfactants can preferably have alkyl chains with eight or more carbon atoms. Exemplary anionic surfactants are linear alkyl sulfonates, and alkylbenzene sulfonates. Exemplary nonionic surfactants are alkylglycosides including alkylglycoside esters such as Crodesta® SL-40® available from Croda, Inc. (New York, N.Y.); alkylglycoside ethers; and alkylpolyethoxylated esters such as Pegosperse® 200 ML available from Glyco Chemicals, Inc. (Greenwich, Conn.) and IGEPAL RC-520® available from Rhone Poulenc Corporation (Cranbury, N.J.).

The first network of fibers 20 of the present disclosure preferably has a basis weight of less than 95 g/m$^2$ and/or less than 75 g/m$^2$ and/or ranging from between about 5 g/m$^2$ and about 95 g/m$^2$ and/or between about 10 g/m$^2$ and about 95 g/m$^2$ and/or between about 10 g/m$^2$ and about 100 g/m$^2$ and/or between about 10 g/m$^2$ and about 75 g/m$^2$.

The first network of fibers 20 of the present disclosure preferably has a density (measured at a 100 g/in$^2$ pressure trap point) of less than about 0.30 g/cm$^3$ and/or less than about 0.25 g/cm$^3$ and/or ranging from about 0.25 g/cm$^3$ to about 0.01 g/cm$^3$ and/or ranging from about 0.20 g/cm$^3$ to about 0.03 g/cm$^3$ and/or ranging from about 0.17 g/cm$^3$ to about 0.04 g/cm$^3$ and/or ranging from about 0.12 g/cm$^3$ to about 0.05 g/cm$^3$.

The first network of fibers 20 of the present disclosure preferably exhibits a total dry tensile strength of less than 8000 g/in and/or less than 5000 g/in and/or less than 3000 g/in and/or less than 2000 g/in and/or less than 1000 g/in and/or less than 800 g/in and/or less than 400 g/in and/or less than 200 g/in and/or less than 100 g/in.

A suitable first network of fibers 20 can be provided as a consumer preferred substrate such as Charmin bath tissue or Bounty paper towels manufactured and sold by the Procter & Gamble Company, Cincinnati, Ohio.

Bonding Layer

The 'bonding layer' generally provides an intermediate layer of material that is used to bond, or assist in bonding, the second network of fibers 30 or the fibers comprising the second network of fibers 30 (discussed infra) to the first network of fibers 20. For example, the intermediate layer of material may comprise a molten material that bonds to the first network of fibers 20 and has sufficient "open" time to allow bonding with the second network of fibers 30 or the fibers comprising the second network of fibers 30. Alternatively, the intermediate layer of material may comprise an adhesive material that is suitable for bonding to both the fibers of the first network of fibers 20 and the fibers comprising the second network of fibers 30.

The bonding layer 40 may be applied to a surface of the first network of fibers 20 as a continuous layer. Alternatively, the bonding layer 40 may be applied to a surface of the first network of fibers 20 to provide any desired pattern of continuous or discontinuous open areas. The bonding layer 40 may also be applied to a surface of the first network of fibers 20 to provide a desired thickness, resiliency, opacity, color, or other attribute that, when combined with the first network of fibers 20 and the fibers of the second network of fibers 30, creates a desired overall absorbent sanitary paper product design. The use of such a bonding layer 40 may enable the use of more economical substrates suitable for use as the first network of fibers 20 by providing a component that delivers some of the desired absorbent sanitary paper product performance while further isolating the first network of fibers 20 from the portion of the absorbent sanitary paper product that will correspond to contact with the user of the absorbent sanitary paper product.

One of skill in the art will understand that the amount of bonding layer 40 that should be applied to a surface of the first network of fibers 20 will likely depend upon the nature and/or structure of the first network of fibers 20, the nature and/or structure of the fibers comprising the second network of fibers 30, the nature and/or characteristics of the adhesive to be so applied, and/or the nature and/or the characteristics of the absorbent sanitary paper product desired.

A wide variety of adhesives can be used to form the bonding layer 40 such as synthetic monomer and synthetic polymer-based adhesives, polyurethanes, acrylics, animal/plant-based adhesives, contact adhesives, plastisols, solvent-type adhesives, natural and synthetic rubber-based resins, and water-based adhesives. By way of example, adhesive suitable for the bonding layer 40 of the present disclosure is a naptha-based adhesive manufactured by Tritech Coatings Corp, St. Louis, Mo. and sold by DonJer Products as Tiotech Flock Adhesive (Product Code: 922-901)

Second Network of Fibers

The properties of low density absorbent sanitary paper products 10 comprising a first network of fibers 20 comprising generally individual fibers, especially cellulose fibers, may be improved by adding a second network of fibers 30 in desired locations. The term 'second network of fibers' describes the totality of individual fibers that are each individually bound to the first network of fibers 20 to form an absorbent sanitary paper product. Preferably, the binding of each fiber comprising the second network of fibers 30 to the first network of fibers 20 can occur through direct mechanical contact with a bonding layer 40 that is disposed upon the first network of fibers 20. It is preferred that the second network of fibers have a total surface area that covers at least about 2% of the total surface area of the first network of fibers.

Alternatively, the binding of each fiber comprising the second network of fibers 30 to the first network of fibers 20 can occur through direct mechanical contact of each fiber comprising the second network of fibers 30 with the fibers disposed upon a surface of the first network of fibers 20 and/or with fibers of the first network of fibers 20 disposed immediately adjacent a surface of the first network of fibers 20 without the need for a bonding layer 40. Such direct contact can be made through the use of chemical bonding (e.g., Hydrogen bonding), mechanical bonding (e.g., penetration of the surface of the first network of fibers 20 by the fibers comprising the second network of fibers 30 with ensuing mechanical engagement and/or entanglement with fibers comprising the first network of fibers 20), electrostatic bonding (e.g., maintaining an electrical and/or static charge differential between the first network of fibers 20 and/or the surface thereof with the fibers comprising the second network of fibers 30), and the like.

The fibers comprising the second network of fibers 30 are generally attached to a surface of the first network of fibers 20 (or to the bonding layer 40 disposed upon the surface of the first network of fibers 20) so they are generally configured to provide the orientation of the longitudinal axis of each fiber in the Z-direction. One of skill in the art will appreciate that at least a majority (i.e., >50%) of the individual fibers comprising the second network of fibers 30 should be generally configured to provide the orientation of the longitudinal axis of each fiber in the Z-direction. The second network of fibers 30 can provide fibers that have a desired geometry (e.g., fiber diameter, length, etc.), physical properties (e.g., flexibility, softness, absorbency, etc.), and/or appearance (e.g., color, texture, reflectivity, opacity, etc.). The fibers comprising the second network of fibers 30 preferably have an average length at least about 20% greater than a fiber comprising the first network of fibers.

The fibers comprising the second network of fibers 30 can be fed into an airstream where they are directed toward one surface of the first network of fibers 20. Before the fibers contact the first network of fibers 20, they can be subjected to an electrostatic charge that orients the fibers comprising the second network of fibers 30 so that their longitudinal axis is generally parallel to the direction of the electrical field and/or the flow of the airstream. The fibers comprising the second network of fibers 30 are then directed into contact with the desired surface to surfaces of the first network of fibers 20. A bonding layer 40 (in the form of an adhesive) can be applied to the desired surface or surfaces of the first network of fibers 20, in any desired pattern, prior to the fibers comprising the second network of fibers 30 contacting the desired surface(s) of the first network of fibers 20.

In other words, fibers comprising the second network of fibers 30 can be disposed upon a surface of the first network of fibers 20 in discrete (i.e., unconnected) regions. In fact, the fibers comprising the second network of fibers 30 can be disposed upon a surface of the first network of fibers 20 in any desired pattern. Such a pattern can be symmetric or asymmetric. In any regard, disposing the fibers comprising the second network of fibers 30 upon a surface of the first network of fibers 20 provides a higher 'localized' basis weight. Stated differently, the regions of the absorbent sanitary paper product where the fibers comprising the second network of fibers 30 are disposed upon a surface of the first network of fibers 20 will have a higher basis weight than the regions of the absorbent sanitary paper product where no fibers comprising the second network of fibers 30 are disposed upon a surface of the first network of fibers 20.

It is envisioned that the oriented fibers of the second network of fibers 30 that contact the bonding layer 40 adhere (i.e., 'stick') thereto. Fibers that do not contact the bonding layer 40 do not stick thereto and can be removed via vacuum in a recycle loop, vibrated, and/or blown off by an air flow. As described supra, the fibers comprising the second network of fibers 30 that adhere to the bonding layer 40 are generally configured so that the longitudinal axis of each fiber is oriented in the Z-direction.

Fibers and fibrous materials constituting the second network of fibers 30 can be provided with characteristics selected to improve specific attributes of the resulting absorbent sanitary paper products 10 described herein. By way of example, this can include, but not be limited to, appearance, thickness, softness, resiliency, absorptive rate or capacity, cleaning, and the like. A wide range of fibrous materials may be used for the second network of fibers 30 to improve the resulting absorbent sanitary paper product, including but not limited to, rayon, nylon, polyester, cellulose, grasses (including bamboo), cotton, starch, and the like. The properties may also be selected, or controlled via processing steps prior to attachment to the first network of fibers 20, to provide desirable characteristics for the absorbent sanitary paper products 10. Properties of the fibers comprising the second network of fibers 30 which may be selected or controlled include, but are not limited to, length, diameter or width, shape (straight, curly, etc.), hydrophilicity, strength, rigidity, flexibility, color, scent, single material vs. a bi-component structure, and the like. Fibers suitable for the second network of fibers 30 include synthetic staple fibers such as rayon fibers (CAS 61788-77-0) and nylon 6, 6-polyamide fibers (CAS 32131-17-2) both available from DonJer Products Corp, Winnebago, Ill. Further it would be possible to provide fibers comprising the second network of fibers 30 to change physical or mechanical properties or characteristics during use.

Further, it may be desired to provide the fibers and fibrous materials constituting the second network of fibers 30 disposed upon the first network of fibers 20 as a plurality of either homogeneous or heterogeneous fibers. In other words, providing the fibers constituting the second network of fibers 30 can be applied to the surface of the first network of fibers 20 as a plurality of individual fibers that can each have a different appearance, thickness, softness, resiliency, absorptive rate or capacity, cleaning, and the like relative to each other. The properties of fibers where the fibers applied to the first network of fibers 20 are heterogeneous can be selected to provide desirable characteristics for the absorbent sanitary paper products 10. Properties of the fibers comprising the second network of fibers 30 which may be selected or controlled include, but are not limited to, length, diameter or width, shape (straight, curly, etc.), hydrophilicity, strength, rigidity, flexibility, color, scent, single material vs. a bi-component structure, and the like. Such properties can be complimentary in appearance and/or function.

Likewise, in another embodiment, the fibers and fibrous materials constituting the second network of fibers 30 can be provided as a plurality of either homogeneous or heterogeneous zones or regions of either homogeneous or heterogeneous fibers. In other words, when it is desired, an absorbent sanitary paper product 10 can be provided with a certain desired functionality. This functionality can be adjusted or derived by providing the second network of fibers 30 as a plurality of discrete regions upon the surface of the first network of fibers 20. These discrete regions can provide the resulting absorbent sanitary paper product 10 with differential properties that can be selected or controlled such as length, diameter or width, shape (straight, curly, etc.), hydrophilicity, strength, rigidity, flexibility, color, scent, single material vs. a bi-component structure, and the like. The properties of each region so applied can be complimentary in appearance and/or function. Each region can also be applied in any desired degree of registration relative to each other or to another characteristic of the resulting absorbent sanitary paper product 10. By way of non-limiting example, the resulting absorbent sanitary paper product 10 could be provided with fibers constituting the second network of fibers 30 to have complementary colors or one zone of cleaning fibers and an adjacent zone with moisture activated scent, or provide certain fibers within the second network of fibers 30 that are moisture activated or bacteria activated.

In yet another embodiment, if the fibers comprising the second network of fibers 30 are selected to be cellulose, it may be preferred to provide the cellulose fibers with different physical properties than the fibers comprising the first network of fibers 20. Further, it may be advantageous to provide the second network of fibers 30 to change physical characteristics during use. By way of non-limiting example, the second network of fibers 30 or the fibers comprising the second network of fibers 30 may change color, or could become curly when placed in contact with water.

Absorbent Sanitary Paper Products

As discussed supra, the fibers comprising the second network of fibers 30 may be attached to the first network of fibers 20 in desired locations. By way of an exemplary but non-limiting embodiment, the fibers comprising the second network of fibers 30 may be attached to either or both faces of the first fiber network. The second network of fibers 30 may be applied in a substantially uniform layer on either or both faces of the first network of fibers 20. Alternatively, the second network of fibers 30 may be attached to the first network of fibers 20 in discrete regions on either or both faces of the first network of fibers 20. In yet another embodiment, the second network of fibers 30 may be applied in a substantially uniform layer on a first face of the first network of fibers 20 and in discrete regions on a second face of the first network of fibers 20.

In yet another exemplary but non-limiting embodiment, the second network of fibers 30 can be provided on either or both outer faces of a plurality of first networks of fiber that are then placed in a face-to-face relationship to form a 2-or-more ply absorbent sanitary paper product. The second network of fibers 30 may be applied in a substantially uniform layer on either or both outer faces of the respective first network of fibers 20. Alternatively, the second network of fibers 30 may be attached to the respective first network of fiber in discrete regions on either or both outer faces.

Alternatively, the second network of fibers 30 may be applied in a substantially uniform layer on one or both inner faces of a plurality of first fiber networks that are placed in a face-to-face relationship to form a 2-or-more ply absorbent sanitary paper product. Alternatively, the second network of fibers 30 may be applied in discrete regions on one or both inner faces of the respective first fiber network. In short, the second network of fibers 30 may be attached in any desired combination of uniform or discrete regions, on any, or all, faces of the plies of the first network of fibers 20 which are then disposed in a face-to-face relationship to form a 2-or-more ply absorbent sanitary paper product.

The second network of fibers 30 may be brought into proximity or into contacting engagement with a surface of the first network of fibers 20 and/or the bonding layer 40 disposed thereon by entraining the constituent fibers comprising the second network of fibers 30 in an airstream by means known in the art. This fiber-laden airstream can then be directed toward and impinge these individual fibers upon a surface of the first network of fibers 20. The impingement of the fibers comprising the second network of fibers 30 upon a surface of the first network of fibers 20 can be selected to occur at any desired point in a manufacturing process. For example, this can include applying the fibers comprising the second network of fibers 30 upon a surface of the first network of fibers 20 before, during, and/or after any ancillary operations to be performed upon the first network of fibers 20 or upon the absorbent sanitary paper product. This can include converting manufacturing operations such as unwinding, cutting, slitting, embossing, laminating, perforating, winding, re-winding, and/or printing.

By way of non-limiting example, the fibers comprising the second network of fibers 30 may be impinged against a surface of a first network of fibers 20 prior to placement of the respective first network of fibers 20 into a face-to-face relationship with another first network of fibers 20 so treated. In other words, a plurality of first networks of fibers, at least one having a second network of fibers 30 disposed thereon can be placed into a face-to-face relationship. This assembly would provide two plies of a first network of fibers 20 in a face-to-face relationship with a second network of fibers 30 disposed therebetween to form an exemplary 2-ply absorbent sanitary paper product.

As envisioned, the fibers comprising the second network of fibers 30 can be brought into proximity or contacting engagement with the first network of fibers 20 electrostatically, under the force of gravity, by the use of a screen or belt, or by applying the fibers comprising the second network of fibers 30 to the first network of fibers 20 from a roll surface having the fibers comprising the second network of fibers 30 disposed thereupon. In any regard, the fibers comprising the second network of fibers 30 can be brought into contacting engagement with a surface of the first network of fibers 20 and/or any bonding layer 40 that may be disposed thereon by controlling the relative position and velocity between the screen or belt and a moving web comprising the first network of fibers 20.

The second network of fibers 30 may be deposited onto a surface of the first fiber network without a bonding layer 40 disposed thereon. This approach may be desirable in applications where mechanical entanglement between the fibers comprising the second network of fibers 30 and the first network of fibers 20 is sufficient. Alternatively, there may be a circumstance when it may be desirable for the subsequent detachment of the fibers comprising the second network of fibers 30 from the first network of fibers 20. This approach may also be used when positioning the second fibers between the two plies comprising a 2-ply product.

Alternatively, the fibers comprising the second network of fibers 30 may be attached to the first network of fibers 20 by hydrogen bonding. Hydrogen bonds between the first network of fibers 20 and the fibers comprising the second network of fibers 30 may be formed by applying relatively small quantities of water in desired locations upon the surface of the first network of fibers 20, followed by deposition or impingement of each fiber of the second network fibers onto the surface of the first network of fibers 20 so treated. The resulting absorbent sanitary paper product can then be dried as may be required.

As discussed supra, the fibers comprising the second network of fibers 30 may be attached to the first network of fibers 20 with a bonding layer 40. One of skill in the art will appreciate that this can involve the application of an adhesive or other adherent to a surface of the first network of fibers 20 in a desired amount and in desired locations. In an exemplary but non-limiting embodiment, polyvinyl alcohol (PVA) in an aqueous solution can be topically applied to discrete regions of the first network of fiber by an applicator such as a permeable roll.

An exemplary permeable roll may be of the type described in U.S. Pat. No. 8,522,711. The permeable roll may be positioned to contact the first network of fibers 20. This web material can be controlled to contact the surface of the permeable roll for a desired portion of the permeable roll circumference. The surface speed of the permeable roll may be controlled to substantially match the speed of the web or the surface speed of the permeable roll may be controlled to a desired speed mismatch with the web speed (e.g. to create a wiping effect). Alternative means for applying adhesive to the first network of fibers 20 may also be used, including but not limited to, spraying, slot dies, gravure printing, offset gravure printing, and other means known in the art.

It has been found that the use of a permeable fluid application roll similar to the type described in U.S. Pat. No. 8,522,711 can be surprisingly effective in applying a fluid, such as an adhesive suitable for bonding layer 40 to the first network of fibers 20. One of the challenges in the application of a bonding layer 40 and providing adherence of a second network of fibers 30 to a through-air-dried (TAD) used to provide the first network of fibers 20 is the relatively low density of the first network of fibers 20 and the relatively large open (or void) spaces between constituent fibers within the first network of fibers 20. Such a permeable roll has been found to be capable of applying relatively large droplets of a fluid (e.g., an adhesive) to the first network of fibers 20. The larger droplet size is believed to bridge across open spaces between constituent fibers within the first network of fibers 20, thereby providing a more effective bonding layer 40 and a corresponding improvement in attachment of the second network of fibers 30 to the first network of fibers 20. Without desiring to be bound by theory, it is believed that providing bonding layer 40 as a relatively high density adhesive can provide an effective means for attaching a second network of fibers 30 to a relatively low density first network of fibers 20. In one embodiment, the ratio of the basis weight of the bonding layer 40 adhesive forming the bonding layer 40 application pattern to the basis weight of the first network of fibers 20 may be at least about 0.5 or at least about 1.0 or at least about 3.0.

One of skill in the art will appreciate that most low-density substrates suitable for use as the first network of fibers 20 are generally difficult to process. Without desiring to be bound by theory, these difficulties can be attributed to the inherent properties of such low density substrates. This can include the fact that such low density substrates can have an irregular topography. Additionally, such low density substrates have a significantly higher stretch profile than non low-density substrates. Further, during converting, such low density substrates exhibit an asymmetrical Poisson effect. In other words, the low density substrates tend to 'neck down' during mechanical processing due to the tensile modulus, caliper, and stretch characteristics (profiles) of the low density web substrate across the width of the web substrate. Such an effect can be observed by one of skill in the art by applying a tension to such a low density substrate in the machine direction by securing the opposing ends of the sheet material, applying a tension, and observing the width of the web substrate change in the cross machine direction as it diverts towards the centerline of the sheet. It has been found that maintaining a consistent, low tension on low density substrates can alleviate these processing difficulties and provide a more uniform first network of fibers, thereby improving the quality of the bonding layer 40 application and the quality of the subsequent application of a second network of fibers 30. In one embodiment, the machine direction tension of the first network of fibers 20 is controlled between about 10 grams per inch and 100 grams per inch by means known in the art during application of the bonding layer 40 and the second network of fibers 30.

It can be preferred that the fibers comprising the second network of fibers 30 may be controlled to impinge upon a surface of the first network of fibers 20 so that the longitudinal axis of the fibers comprising the second network are substantially perpendicular (i.e., the Z-direction) to the plane comprising the first fiber network (i.e., machine direction and cross-machine direction). This result can be achieved by using a process known to one of skill in the art as flocking. Flocking can be used to impart a decorative and/or functional characteristic(s) to a substrate or surface. Most commonly, flocking refers to the process of applying a fiber, which can be synthetic or natural, to another substrate or surface that has been coated with an adhesive. Some of the more common fibers used for the fibers comprising the second network of fibers 30 include rayon, nylon, polyester, and cotton. One of skill in the art will recognize that flocking can be accomplished by applying the fibers comprising the second network of fibers 30 to the first network of fibers 20 electrostatically, using a beater bar/gravity/vacuum, by spraying, and/or using transfers.

In the case of electrostatic flocking, the fiber to be flocked (i.e., the fibers comprising the second network of fibers 30) is given a charge. This can often require that the fiber be suitably treated to make it electrically conductive. An example of a suitable treatment is "Floctan®" from S. A. Ajinomoto OmniChem N.V., OmniChem NaturalSpecialities, Parc Scientifique Fleming, B 1348 Louvain-la-Neuve, Belgium. Pretreated fibers are available commercially. This includes Suede-Tex® Rayon fibers available from DonJer Products Corporation, 13142 Murphy Road Winnebago, Ill. 61088 or Chopped White Cotton Flock available from International Fiber Corporation, North Tonawanda, N.Y.

By way of non-limiting example, one of skill in the art will understand the electrostatic flocking process to utilize a high-voltage electric field generated between two probes that provide the fibers comprising the second network of fibers 30 with a positive charge. Concurrently, the surface/area disposed under the first network of fibers 20 is given a negative charge or can be grounded. Here, the fibers comprising the second network of fibers 30 traverse along the electric field vertically and can embed into adhesive disposed upon the first network of fibers 20. As the fibers comprising the second network of fibers 30 impinge upon the adhesive, they are largely disposed in an orientation perpendicular to the surface of the first network of fibers 20. However, one of skill in the art will recognize that adjusting the angle of the electric field relative to the surface of the first network of fibers 20 can provide any desired angle of impingement relative to the longitudinal axis of each fiber of the second network of fibers 30 relative to the surface of the first network of fibers 20. This process can form a highly dense, generally uniform flock coating. By controlling/varying the electric field strength and/or intensity, and the speed of the flocking process, the thickness of the fibers comprising the second network of fibers 30 disposed upon the first network of fibers 20 can be controlled. It is believed that the fibers comprising the second network of fibers 30 in the impinging airstream not contacting the adhesive disposed upon a surface of the first network of fibers 20 will, accordingly, not be attached to the first network of fibers 20. Any unattached fibers comprising the second network of fibers 30 may be removed via vacuum means known in the art and may be recycled and subsequently attached to the first network of fibers 20 in other locations.

An alternative process provides for the deposition of fibers comprising the second network of fibers 30 upon a surface of a first network of fibers 20 having a bonding layer 40 adhesive disposed in desired regions of the surface of the first network of fibers 20 using any technique including the permeable roll described supra. The fibers comprising the second network of fibers 30 are subsequently impinged against the surface of the first fiber network with Dan-Web air-laying equipment. Here, a portion of the fibers comprising the second network of fibers 30 are entrained in an impinging airstream and can then contact the adhesive disposed upon a surface of the first network of fibers 20 and become attached thereto. The longitudinal axis of the fibers comprising the second network of fibers 30 may be oriented to be substantially random relative to the plane comprising the first network of fibers 20. Alternatively, the longitudinal axis of the fibers comprising the second network of fibers 30 may be oriented to be substantially parallel relative to the plane comprising the first network of fibers 20.

In yet another alternative process, a combination of flocking and Dan-Web® air-laying equipment may be used to provide any desired combination of regions comprising secondary network of fibers 30 wherein some of the regions comprise secondary fibers primarily disposed with the longitudinal axis of the secondary fibers perpendicular to the plane comprising the first network of fibers 20 and other regions comprise secondary fibers primarily disposed with the longitudinal axis of the secondary fibers randomly oriented or parallel to the plane comprising the first network of fibers 20.

The second network of fibers 30 can be sub-divided into regions that can be disposed upon the first network of fibers 20 in a manner that provides the registration of these discrete regions in registration with other features disposed upon or within the first network of fibers 20. These features disposed within or upon the first network of fibers 20 can include, but not be limited to, embossing, printing, softness or other fluid based performance regions, perforations, sheet edges, and the like. This registration of each discrete region of the second network of fibers 30 may be controlled by measurement and control of the axial and circumferential positions of the adhesive applicator relative to the corresponding surface of the first network of fibers 20. For example, a permeable adhesive application roll can be rotated relative to the axial and circumferential positions of the process rolls imparting these other product features disposed upon or within the first network of fibers 20 by means known in the art.

One of skill in the art will recognize that the absorbent sanitary paper product can be pre-processed and/or further processed as may be required to provide a consumer-relevant absorbent sanitary paper product. Such additional processing can include embossing, printing, perforating, slitting, folding, winding, combinations thereof, and the like. In any regard, it is believed that the absorbent sanitary paper product can be provided in a form that is suitable for immediate consumer use within the house and/or for use with ordinary household chores and/or tasks.

EXAMPLE 1

Referring again to FIG. 1, the first network of fibers 20 of absorbent sanitary paper product 10 is formed by a 3% by weight aqueous slurry of NSK (northern softwood Kraft) and is made in a conventional re-pulper. The NSK slurry is refined, and a 2% solution of Kymene 557LX is added to the NSK stock pipe at a rate sufficient to deliver 1% Kymene 557LX by weight of the dry fibers. The absorption of the wet strength resin is enhanced by passing the treated slurry though an in-line mixer. KYMENE® 557LX is supplied by Hercules Corp. of Wilmington, Del. A 1% solution of carboxy methyl cellulose is added after the in-line mixer at a rate of 0.15% by weight of the dry fibers to enhance the dry strength of the fibrous structure. The aqueous slurry of NSK fibers passes through a centrifugal stock pump to aid in distributing the Carboxy Methyl Cellulose (CMC). An aqueous dispersion of DiTallow DiMethyl Ammonium Methyl Sulfate (DTDMAMS) (170° F./76.6° C.) at a concentration of 1% by weight is added to the NSK stock pipe at a rate of about 0.05% by weight DTDMAMS per ton of dry fiber weight.

A 3% by weight aqueous slurry of eucalyptus fibers is made in a conventional re-pulper. A 2% solution of Kymene® 557LX is added to the eucalyptus stock pipe at a rate sufficient to deliver 0.25% Kymene® 557LX by weight of the dry fibers. The absorption of the wet strength resin is enhanced by passing the treated slurry though an in-line mixer.

The NSK fibers are diluted with white water at the inlet of a fan pump to a consistency of about 0.15% based on the total weight of the NSK fiber slurry. The eucalyptus fibers, likewise, are diluted with white water at the inlet of a fan pump to a consistency of about 0.15% based on the total weight of the eucalyptus fiber slurry. The eucalyptus slurry and the NSK slurry are directed to a multi-channeled headbox suitably equipped with layering leaves to maintain the streams as separate layers until discharged onto a traveling Fourdrinier wire. A three-chambered headbox is used. The eucalyptus slurry containing 65% of the dry weight of the tissue ply is directed to the chamber leading to the layer in contact with the wire, while the NSK slurry comprising 35% of the dry weight of the ultimate tissue ply is directed to the chamber leading to the center and inside layer. The NSK and eucalyptus slurries are combined at the discharge of the headbox into a composite slurry.

The composite slurry is discharged onto the traveling Fourdrinier wire and is dewatered assisted by a deflector and vacuum boxes. The Fourdrinier wire is of a 5-shed, satin weave configuration having 105 machine-direction and 107 cross-machine-direction monofilaments per inch. The speed of the Fourdrinier wire is about 800 fpm (feet per minute).

The embryonic wet web is dewatered to a consistency of about 15% just prior to transfer to a patterned drying fabric made in accordance with U.S. Pat. No. 4,529,480. The speed of the patterned drying fabric is the same as the speed of the Fourdrinier wire. The drying fabric is designed to yield a pattern-densified tissue with discontinuous low-density deflected areas arranged within a continuous network of high density (knuckle) areas. This drying fabric is formed by casting an impervious resin surface onto a fiber mesh supporting fabric. The supporting fabric is a 45×52 filament, dual layer mesh. The thickness of the resin cast is about 0.009 inches above the supporting fabric. The drying fabric for forming the paper web has about 562 discrete deflection regions per square inch. The area of the continuous network is about 50 percent of the surface area of the drying fabric.

Further dewatering is accomplished by vacuum assisted drainage until the web has a fiber consistency of about 25%. While remaining in contact with the patterned drying fabric, the web is pre-dried by air blow-through pre-dryers to a fiber consistency of about 65% by weight. The web is then adhered to the surface of a Yankee dryer, and removed from the surface of the dryer by a doctor blade at a consistency of about 97 percent. The Yankee dryer is operated at a surface speed of about 800 feet per minute. The dry web is passed through a rubber-on-steel calendar nip. The dry web (i.e., first network of fibers 20) is wound onto a roll at a speed of 680 feet per minute to provide dry foreshortening of about 15 percent.

The exemplary absorbent sanitary paper product 10 was produced with a CP 70 Electrostatic Flocker (AC/DC unit). The fibers comprising the second network of fibers 30 were provided as Suede-Tex® Rayon Fibers. Clear adhesive from the Donjer Company was used as a bonding layer 40 to adhere the fibers comprising the second network of fibers to a surface of the first network of fibers.

Figure 7:
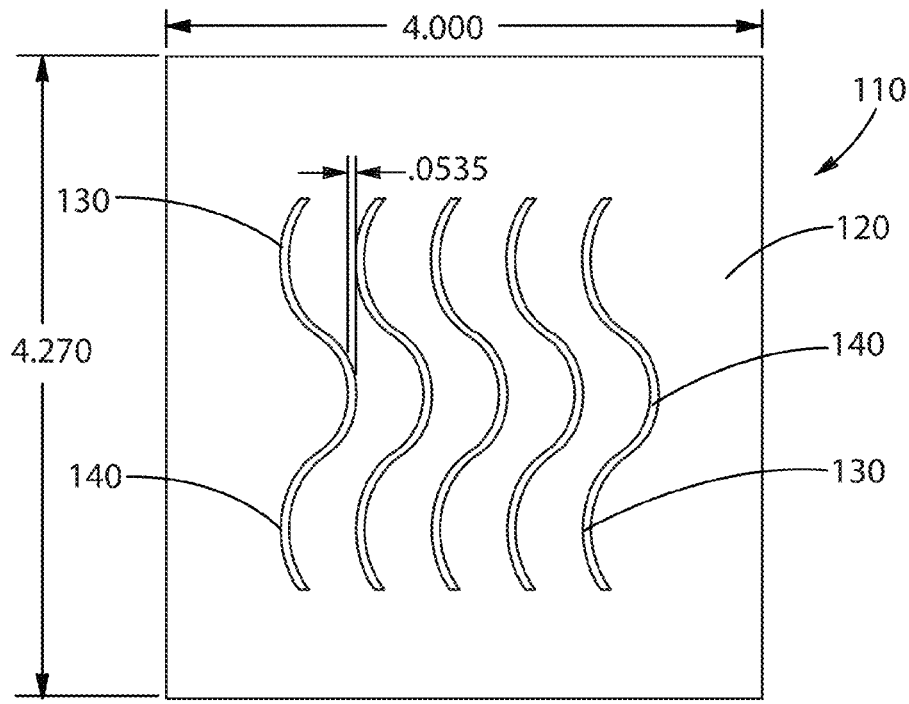
FIG. 7 is a plan view of an exemplary pattern suitable for disposing a second network of fibers and/or a bonding layer upon a first network of fibers to form an exemplary absorbent sanitary paper product; and, FIG. 8 is a plan view of another exemplary pattern suitable for disposing a second network of fibers and/or a bonding layer upon a first network of fibers to form another exemplary absorbent sanitary paper product.
Figure 8:
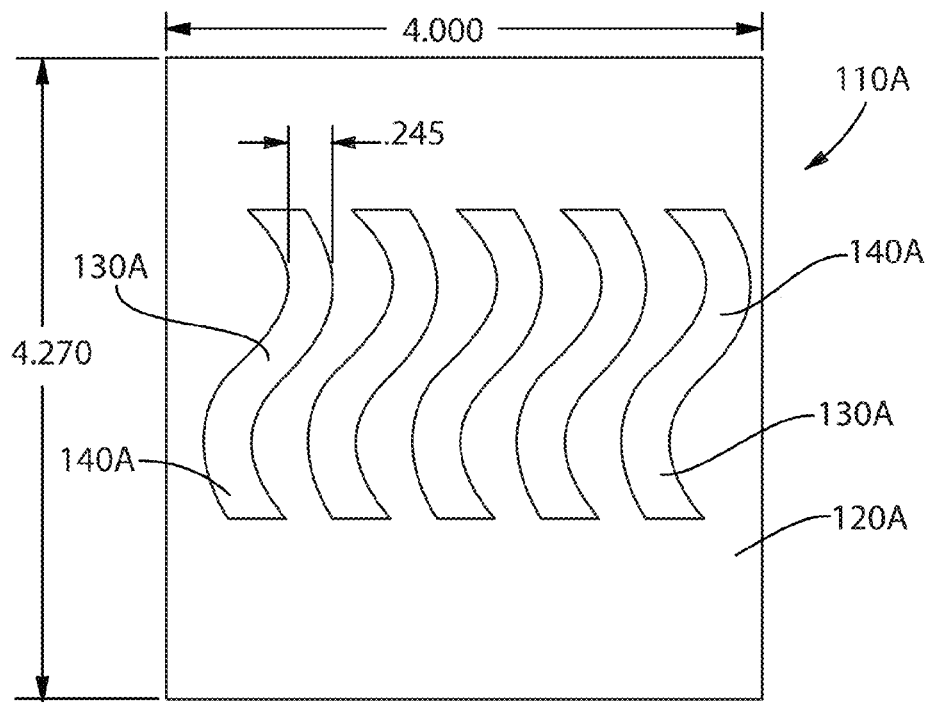

The adhesive was applied to the first network of fibers in a pattern using a fine mesh screen stencil from Victory Factory 184-10 Hollis, N.Y. 11423 (i.e., using a 230 mesh count with 60 micron mesh openings). The substrate comprising the first network of fibers was placed upon a metal plate constituting the ground of the electric field generating system. The stencil was then placed upon one surface of the substrate. Next, the adhesive was placed upon a plastic shim and the shim was then slid across the mesh screen stencil to apply the adhesive through the stencil onto the surface of the substrate. In this example, about 0.3 grams of adhesive per square inch were applied within the application pattern area. The amount of adhesive applied to the first network of fibers may be controlled to achieve desired properties including, but not limited to, quantity of second network fibers, density of second network fibers, appearance of second network fibers, pattern and area of second network fibers, or related effects on the properties of the first network of fibers such as softness, absorbency, and the like. The add-on weight of the adhesive may also vary significantly based on the type of adhesive used. The adhesive add-on weight may range from 0.2 to 0.4 grams per square inch within the application pattern area, or from 0.1 to 0.5 grams per square inch within the application pattern area, or from 0.01 to 5 grams per square inch within the application pattern area. FIGS. 7 and 8 depict exemplary patterns suitable for use for the deposition of the bonding layer 140, 140A and/or a second network of fibers 130, 130A upon a first network of fibers 120, 120A to form exemplary absorbent sanitary paper product 110, 11A.

Once the adhesive has been applied to a surface of the first network of fibers and the stencil removed, a flocking wand (in combination with the plate discussed supra that form the desired electric field therebetween) can be used. The ground of the power supply of the flocking wand was electrically connected to the metal plate/surface. The flock fiber (the fibers comprising the second network of fibers) was placed into the chamber of the flocking wand. A voltage of about 60 KV was applied to the fibers disposed within the flocking wand. The flocking wand was then waved about 1 inch above the surface of the substrate comprising the first network of fibers.

The fibers comprising the second network of fibers travelled through the electric field and embedded into the adhesive disposed upon the first network of fibers in a largely perpendicular orientation to the surface of the first network of fibers. The adhesive disposed upon the first network of fibers and having the fibers comprising the second network of fibers disposed therein was allowed to dry. The resulting absorbent sanitary paper product substrate was then shaken to remove any un-bonded fibers. The resulting absorbent sanitary paper product exhibited patterned and adhered flock fibers upon the surface of the substrate. The amount of fibers comprising the second network of fibers disposed upon the first network of fibers was about 0.07 grams per square inch within the application pattern area. The amount of second network fibers applied to the first network of fibers may be controlled to achieve desired properties including, but not limited to, quantity of second network fibers, density of second network fibers, appearance of second network fibers, pattern and area of second network fibers, or related effects on the properties of the first network of fibers such as softness, absorbency, appearance, cleaning properties, and the like. The add-on weight of the second network fibers may also vary significantly based on the type of second network fibers used. The second network fiber add-on weight may range from 0.04 to 0.11 grams per square inch within the application pattern area, or from 0.02 to 0.25 grams per square inch within the application pattern area, or from 0.001 to 5 grams per square inch within the application pattern area.

EXAMPLE 2

The first network of fibers for Example 2 were made according to the process detailed in Example 1 supra. Two plies were combined with the wire side facing out. A bonding layer adhesive was applied to a surface of the manufactured first network of fibers as detailed in Example 1 supra.

In this example, the fibers comprising the second network of fibers were controlled to impinge upon a surface of the first network of fibers so that the longitudinal axis of the fibers comprising the second network of fibers were oriented randomly relative to the MD/CD plane of the first network of fibers with an applicator manufactured by Dan-Web Machinery A/S, Risskov, Denmark. The airstream carrying the fibers comprising the second network of fibers impinged the fibers comprising the second network of fibers against a surface of the first network of fibers to form an exemplary absorbent sanitary paper product substrate.

EXAMPLE 3

Figure 2:
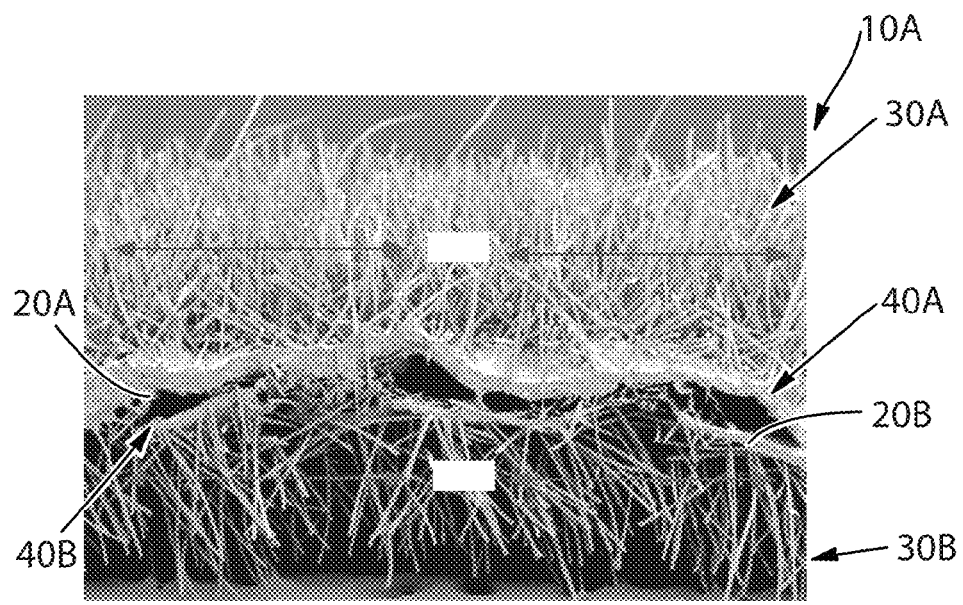
FIG. 2 is a photomicrograph showing a cross-sectional view of another exemplary absorbent sanitary paper product of the present disclosure detailing the first network of fibers, bonding layer, and second network of fibers applied thereto.
Figure 3:
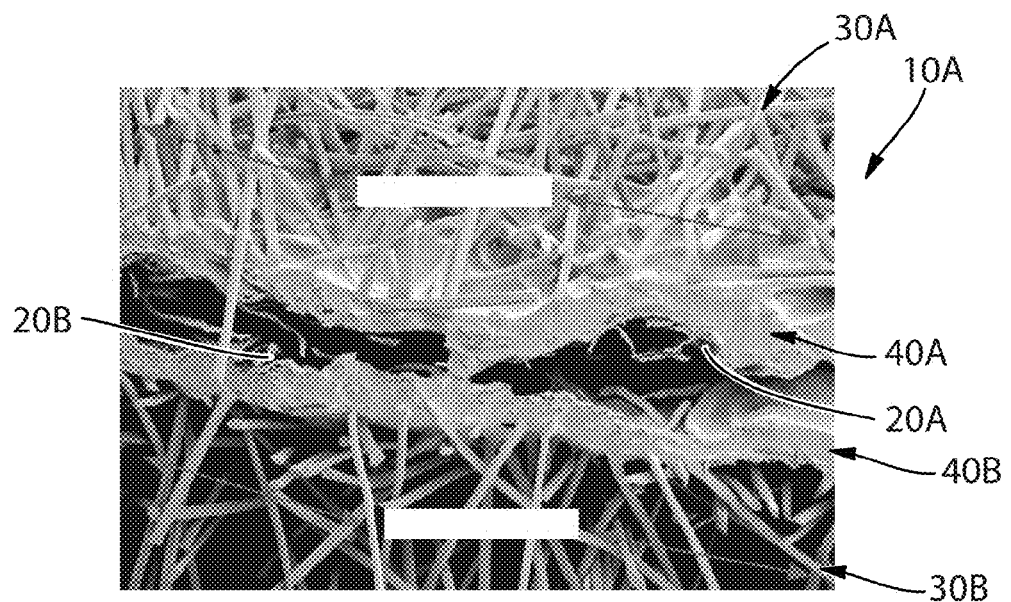
FIG. 3 is a photomicrograph showing the surface of yet another exemplary absorbent sanitary paper product of the present disclosure detailing the first network of fibers and second network of fibers applied to a surface of the first network of fibers in a discontinuous pattern as discussed herein.

Referring to FIGS. 2 and 3, two individual plies for Example 3, forming an absorbent sanitary paper product 10A (each comprising a first network of fibers 20A, 20B, a second network of fibers, 30A, 30B, and a respective bonding layers 40A, 40B) were each made according to the process detailed in Example 1 supra. The two plies were combined in a face-to-face relationship with the second network of fibers 30A, 30B (i.e., flocked sides) facing outward.

Figure 4:
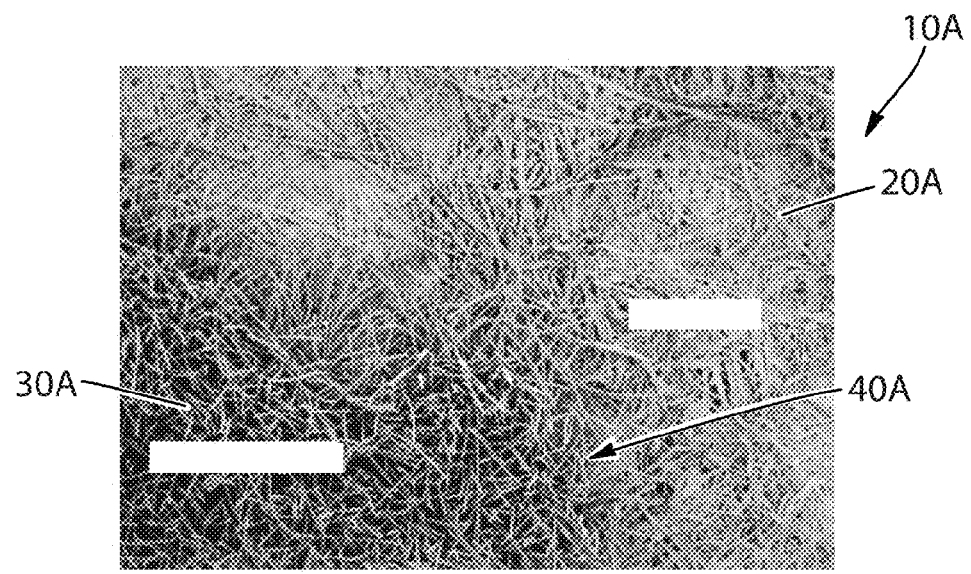
FIG. 4 is a photomicrograph showing a cross-sectional view of still another exemplary 2-ply absorbent sanitary paper product of the present disclosure detailing the first network of fibers, bonding layer, and second network of fibers applied thereto.

Referring to FIG. 4, the resulting pattern of the fibers comprising the second network of fibers 30A are shown disposed upon a surface of the first network of fibers 20A in a non-random, continuous pattern upon the surface of the first network of fibers 20A to form absorbent sanitary paper product 10A. The bonding layer 40A is provided upon the surface of the first network of fibers 20A in the pattern desired for the application of the fibers comprising the second network of fibers 30A thereto.

EXAMPLE 4

Two individual plies of absorbent sanitary paper product for Example 4 were each made according to the process detailed in Example 1 supra. The two plies were combined in a face-to-face relationship with the flocked side facing inward.

EXAMPLE 5

Figure 5:
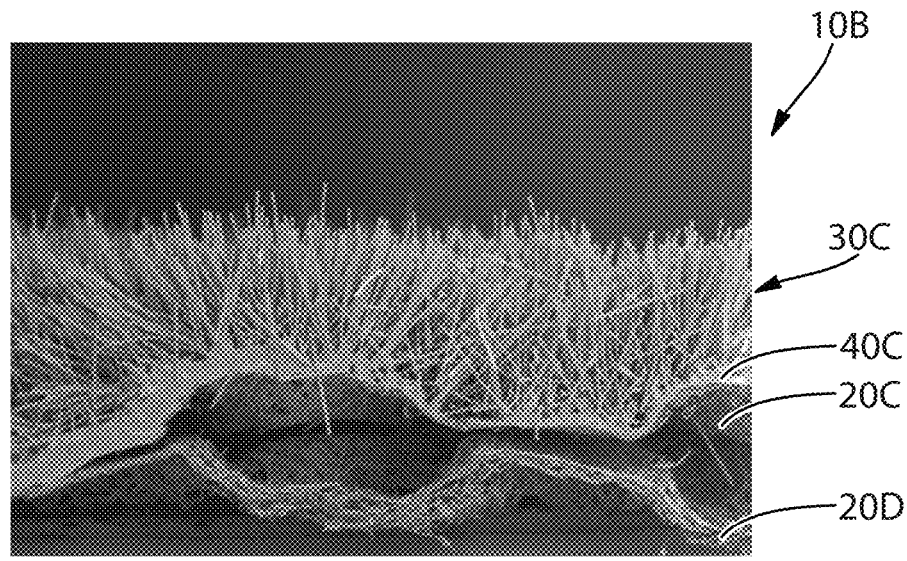
FIG. 5 is a photomicrograph showing a cross-sectional view of yet still another exemplary 2-ply absorbent sanitary paper product of the present disclosure detailing the first network of fibers, bonding layer, and second network of fibers applied in discrete regions thereto.
Figure 6:
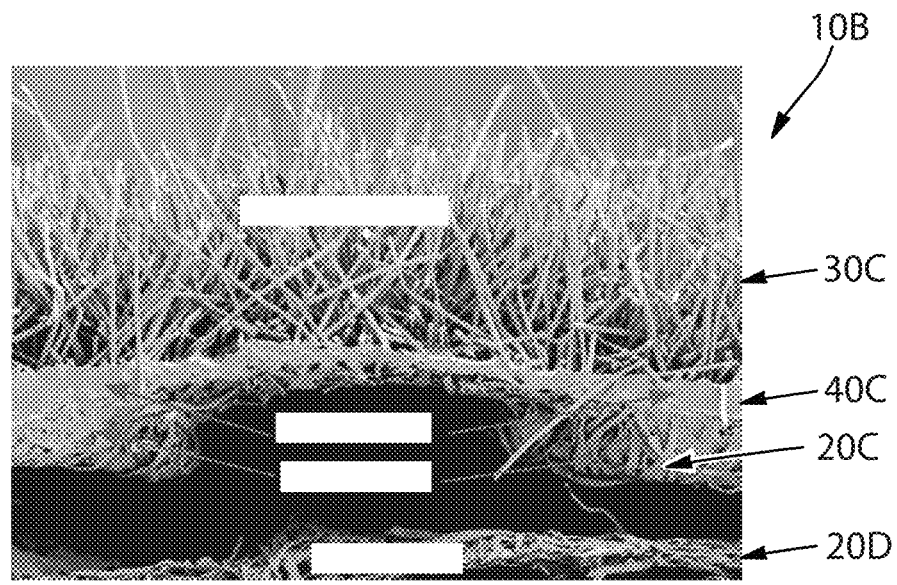
FIG. 6 is a photomicrograph showing a cross-sectional view of yet another exemplary 2-ply absorbent sanitary paper product of the present disclosure detailing the first network of fibers, bonding layer, and second network of fibers applied continuously thereto.

Referring to FIGS. 5 and 6, one individual ply of absorbent sanitary paper product 10B of Example 5 having a first network of fibers 20C, bonding layer 40C, and second network of fibers 30C was made according to the process detailed in Example 1 supra. The ply was the combined in a face-to-face relationship with an un-treated (i.e., un-flocked) ply (e.g., a second first network of fibers 30D) produced according to Example 1 with the second network of fibers 30C (i.e., flocked) side facing outward.

Analytical and Testing Procedures

The following test methods are representative of the techniques utilized to determine the physical characteristics of the multi-ply tissue product associated therewith.

1. Sample Conditioning and Preparation

Unless otherwise indicated, samples are conditioned according to Tappi Method #T402OM-88. Paper samples are conditioned for at least 2 hours at a relative humidity of 48 to 52% and within a temperature range of 22° to 24° C. Sample preparation and all aspects of testing using the following methods are confined to a constant temperature and humidity room.

2. Basis Weight

The basis weight of all samples of the first network of fibers 20 were measured in accordance with Tappi test method T410 om-08 entitled "Grammage of paper and paperboard".

3. Compressibility

Thickness (measured in mils, 0.001 inch) is measured as a function of confining pressure (g/in$^2$) using a Thwing-Albert (14 W. Collings Ave., West Berlin, N.J.) Vantage Compression/Softness Tester (model 1750-2005 or similar), equipped with a 2500 g load cell (force accuracy is +/−0.25% when measuring value is between 10%-100% of load cell capacity, and 0.025% when measuring value is less than 10% of load cell capacity), a 1.128 inch diameter steel pressure foot (one square inch cross sectional area) which is aligned parallel to the steel anvil (2.5 inch diameter). The pressure foot and anvil surfaces must be clean and dust free, particularly when performing the steel-to-steel test. Thwing-Albert software (MAP) controls the motion and data acquisition of the instrument.

The instrument and software is set-up to acquire crosshead position and force data at a rate of 50 points/sec. The crosshead speed (which moves the pressure foot) for testing samples is set to 0.10 inches/min (the steel-to-steel test speed is set to 0.05 inches/min) Crosshead position and force data are recorded between the load cell range of approximately 5 and 1525 grams during compression of this test. Since the foot area is one square inch, the force data recorded corresponds to pressure in units of g/in$^2$. The MAP software is programmed to report 12 crosshead position values at specific pressure trap points (PTP) of 100, 125, 150, 200, 300, 400, 500, 600, 750, 1000, 1250, and 1500 g/in$^2$ (i.e., recording the crosshead position of very next acquired data point after the each pressure point trap is surpassed).

Since the overall test system, including the load cell, is not perfectly rigid, a steel-to-steel test is performed (i.e., nothing in between the pressure foot and anvil) at least twice for each batch of testing, to obtain an average set of steel-to-steel crosshead positions at each of the 12 trap points. This steel-to-steel crosshead position data is subtracted from the corresponding crosshead position data at each trap point for each tested sheet sample, thereby resulting in the sheet thickness (mils) at each pressure trap point.

$$\text{Sheet}T(\text{trap}) = \text{Sheet}CP(\text{trap}) - \text{Steel}CP(\text{trap})$$

where:

trap=trap point pressure

SheetT=Thickness of sheet (at trap pressure)

SheetCP=Crosshead position of sheet in test (at trap pressure)

SteelCP=Crosshead position of steel-to-steel test (at trap pressure)

The test sample is cut to a size no larger than about 4 inch by 4 inch, and no smaller than the area of the pressure foot (about 1.25 inch by 1.25 inch). The area to be tested for compressibility (i.e., that which is to be contacted by the pressure foot) must be free of flocked material (so that only the base material is tested). While handling the sample, the test region of the sample (where the pressure foot contacts) must never be physically touched, stretched, or strained.

The sample is laid flat on the lower anvil, positioned such that the pressure foot does not contact any flocked material (if present on the sheet), and then the test is initiated (via the MAP software). From the test, the crosshead position of the sheet at each trap pressure is determined. This testing is repeated on a minimum of 3 replicate sheet samples per condition, in order to calculate an average crosshead position of the sheet at each trap pressure (i.e., SheetCP(trap)). Then, using the average steel-to-steel crosshead trap points (i.e., SteelCP(trap)), the average sheet thickness at each trap (i.e., SheetT(trap) is calculated, and reported to the nearest 0.01 mils.

4. Density

The density (D) of a multi-layered tissue paper, as that term is used herein, is the average density calculated as the basis weight of that paper divided by the average sheet thickness at each pressure point trap (PTP) determined from the Compressibility test method described supra, with the appropriate unit conversions incorporated therein. Results are reported in g/cm$^3$.

5. Dry Tensile

Tensile strength was measured according to Tappi method T 494 om-06, with exceptions and/or clarifications as follows: strip width=1.00 inches; gauge length=2.0 inches; rate of jaw separation=1.0 inch/min 4 strips are tested in the MD, and 4 strips tested in the CD. The average tensile strength for each direction is calculated, and the sum of these two values is reported as the "Total Dry Tensile Strength" of the sample, reported in units of grams force per inch sample width (g$_f$/in), to the nearest 1 g$_f$/in.

Results

The first network of fibers of the absorbent sanitary paper products 10 produced above in Examples 1-5, as well as several exemplary and commercially available absorbent sanitary paper products 10 suitable for the first network of fibers were tested using the test methods described supra. The results of this testing data are presented below in Tables 1 and 2.

TABLE 1

Exemplary density values for products suitable for the first network of fibers

| Sample | Density, D, (g/cc) calculated at various PTP values | | | | | | | | | | | |
|---|---|---|---|---|---|---|---|---|---|---|---|---|
| | D@100 PTP | D@125 PTP | D@150 PTP | D@200 PTP | D@300 PTP | D@400 PTP | D@500 PTP | D@600 PTP | D@750 PTP | D@1000 PTP | D@1250 PTP | D@1500 PTP |
| 7th Gen Towel | 0.0737 | 0.0760 | 0.0777 | 0.0810 | 0.0867 | 0.0920 | 0.0963 | 0.1012 | 0.1078 | 0.1216 | 0.1356 | 0.1522 |
| Bounty Duratowel | 0.0684 | 0.0706 | 0.0726 | 0.0762 | 0.0827 | 0.0887 | 0.0941 | 0.0992 | 0.1060 | 0.1166 | 0.1257 | 0.1343 |

TABLE 1-continued

Exemplary density values for products suitable for the first network of fibers

Density, D, (g/cc) calculated at various PTP values

| Sample | D@100 PTP | D@125 PTP | D@150 PTP | D@200 PTP | D@300 PTP | D@400 PTP | D@500 PTP | D@600 PTP | D@750 PTP | D@1000 PTP | D@1250 PTP | D@1500 PTP |
|---|---|---|---|---|---|---|---|---|---|---|---|---|
| Charmin Basic | 0.1003 | 0.1041 | 0.1069 | 0.1121 | 0.1194 | 0.1249 | 0.1288 | 0.1333 | 0.1378 | 0.1457 | 0.1518 | 0.1577 |
| Charmin Ultra Strong | 0.0784 | 0.0807 | 0.0827 | 0.0862 | 0.0921 | 0.0970 | 0.1012 | 0.1051 | 0.1102 | 0.1185 | 0.1250 | 0.1320 |
| Scott 1000 | 0.1089 | 0.1174 | 0.1253 | 0.1420 | 0.1630 | 0.1734 | 0.1788 | 0.1840 | 0.1911 | 0.1996 | 0.2068 | 0.2112 |
| Wasserstrom hand towel | 0.1636 | 0.1714 | 0.1794 | 0.1943 | 0.2195 | 0.2345 | 0.2418 | 0.2497 | 0.2559 | 0.2687 | 0.2750 | 0.2815 |
| Flocked pink wallpaper | 0.7154 | 0.7261 | 0.7313 | 0.7407 | 0.7517 | 0.7610 | 0.7638 | 0.7684 | 0.7714 | 0.7848 | 0.7898 | 0.7921 |
| Flocked white Velvet paper | 0.3479 | 0.3575 | 0.3635 | 0.3718 | 0.3853 | 0.3941 | 0.4001 | 0.4057 | 0.4111 | 0.4218 | 0.4293 | 0.4356 |

TABLE 2

Exemplary Total Dry Tensile Strength and Basis Weight (BW) values for products suitable for the first network of fibers

| Sample | Total Dry Tensile Strength (g/in) | BW (g/m$^2$) |
|---|---|---|
| Bounty Duratowel (2-ply) | 2356 | 63.3 |
| Charmin Basic (1-ply) | 657 | 34.3 |
| Charmin Ultra Strong (2-ply) | 705 | 40.7 |
| Scott 1000 (1-ply) | 635 | 17.8 |
| Wasserstrom hand towel (1-ply) | 2353 | 33.2 |
| Flocked pink wallpaper | 29667 | 166.0 |
| Flocked white Velvet paper | 10204 | 108.9 |

The dimensions and values disclosed herein are not to be understood as being strictly limited to the exact dimension and values recited. Instead, unless otherwise specified, each such dimension and/or value is intended to mean both the recited dimension and/or value and a functionally equivalent range surrounding that dimension and/or value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of manufacturing an absorbent sanitary paper product having a machine direction, a cross-machine direction orthogonal and co-planar thereto, and a Z-direction orthogonal to both the machine- and cross-machine directions, said method comprising the steps of:
   providing a first first network of fibers having opposing first and second sides, each fiber of said first first network of fibers having a longitudinal axis generally disposed within the plane comprising the machine- and cross-machine-directions;
   providing a second first network of fibers having opposing first and second sides, each fiber of said second first network of fibers having a longitudinal axis generally disposed within the plane comprising the machine- and cross-machine-directions;
   applying a first bonding layer in a first pattern to said first side of said first first network of fibers;
   applying a second bonding layer in a second pattern to said first side of said first first network of fibers;
   applying a first second network of fibers to said first bonding layer, each individual fiber comprising said second network of fibers having a longitudinal axis generally disposed in the Z-direction;
   applying a second second network of fibers to said second bonding layer, each individual fiber comprising said second second network of fibers having a longitudinal axis generally disposed in the Z-direction, said first second network of fibers and said second second network of fibers being different; and,
   placing said second side of said first first network of fibers and said second side of said second first network of fibers into contacting engagement.

2. The method of claim 1 further comprising the step of:
   applying a third second network of fibers to said second bonding layer, each individual fiber comprising said third second network of fibers having a longitudinal axis generally disposed in the Z-direction.

3. The method of claim 1 wherein, prior to said step of placing said second side of said first first network of fibers and said second side of said second first network of fibers into contacting engagement, applying an adhesive to one of said second side of said first first network of fibers and said second side of said second first network of fibers.

4. The method of claim 1 further comprising the step of:
   further processing said absorbent sanitary paper product with a process selected from the group consisting of embossing, printing, perforating, slitting, folding, winding, combinations thereof, and the like.

5. A method of manufacturing an absorbent sanitary paper product having a machine direction, a cross-machine direction orthogonal and co-planar thereto, and a Z-direction orthogonal to both the machine- and cross-machine directions, said method comprising the steps of:
   providing a first first network of fibers having opposing first and second sides, each fiber of said first first network of fibers having a longitudinal axis generally disposed within the plane comprising the machine- and cross-machine-directions;

providing a second first network of fibers having opposing first and second sides, each fiber of said second first network of fibers having a longitudinal axis generally disposed within the plane comprising the machine- and cross-machine-directions;

applying a first bonding layer to said first side of said first first network of fibers;

applying a first second network of fibers to a first region of said first bonding layer, each individual fiber comprising said first second network of fibers having a longitudinal axis generally disposed in the Z-direction;

applying a second second network of fibers to a second region of said first bonding layer, each individual fiber comprising said second second network of fibers having a longitudinal axis generally disposed in the Z-direction, said first region of said bonding layer being disposed adjacent said second region of said bonding layer, said first second network of fibers and said second second network of fibers being different; and, placing said second side of said first first network of fibers and said second side of said second first network of fibers into contacting engagement.

6. The method of claim 5 wherein said step of applying said first bonding layer to said first side of said first first network of fibers further comprises the step of:

applying said first bonding layer to said first side of said first first network of fibers in a pattern.

7. The method of claim 6 wherein said step of applying said first bonding layer to said first side of said first first network of fibers in a pattern further comprises the step of:

applying said first bonding layer in a plurality of discrete regions upon said first side of said first first network of fibers.

8. The method of claim 6 wherein said step of applying said second bonding layer to said first side of said second first network of fibers further comprises the step of:

applying said second bonding layer to said first side of said second first network of fibers in a pattern.

9. The method of claim 5 wherein, prior to said step of placing said second side of said first first network of fibers and said second side of said second first network of fibers into contacting engagement, applying an adhesive to one of said second side of said first first network of fibers and said second side of said second first network of fibers.

10. The method of claim 5 further comprising the step of:

further processing said absorbent sanitary paper product with a process selected from the group consisting of embossing, printing, perforating, slitting, folding, winding, combinations thereof, and the like.

* * * * *